United States Patent [19]

Martell et al.

[11] Patent Number: 5,114,688
[45] Date of Patent: May 19, 1992

[54] BINUCLEAR METAL MACROCYCLIC AND MACROBICYCLIC COMPLEXES FOR OXYGEN SEPARATION AND TRANSPORT

[75] Inventors: Arthur E. Martell; Ramunas J. Motekaitis, both of College Station, Tex.

[73] Assignee: L'Air Liquide, Societe Anonyme Pour l'Etude et Exploitation des Procedes Georges Claude, Paris, France

[21] Appl. No.: 468,938

[22] Filed: Jan. 23, 1990

[51] Int. Cl.$^5$ .................. C01B 13/00; C07F 1/08; C07F 13/00; C07F 15/02
[52] U.S. Cl. ............................ 423/219; 423/579; 556/45; 556/110; 556/138
[58] Field of Search ............... 556/50, 116, 140, 45, 556/110, 138; 423/219, 579

[56] References Cited

U.S. PATENT DOCUMENTS

| | | |
|---|---|---|
| 2,450,276 | 9/1948 | Fogler et al. .................. 423/219 |
| 3,432,574 | 3/1969 | Kamal ........................... 556/50 |
| 4,032,617 | 6/1977 | Gay ............................... 423/219 |
| 4,542,010 | 9/1985 | Roman et al. .................. 423/219 |
| 4,680,037 | 7/1987 | Ramprasad et al. ........... 423/219 |
| 4,735,634 | 4/1988 | Norman et al. ................ 423/219 |
| 4,746,748 | 5/1988 | Aoki et al. ...................... 556/34 |

Primary Examiner—Wayne A. Langel
Attorney, Agent, or Firm—Oblon, Spivak, McClelland, Maier & Neustadt

[57] ABSTRACT

A binuclear metal complex, comprising a metal-complexed ligand which ligand is formed by the reaction of a dialdehyde and a poly primary amine, which complex is capable of reacting reversibly with molecular oxygen.

12 Claims, 6 Drawing Sheets

BINUCLEAR METAL MACROCYCLIC AND MACROBICYCLIC COMPLEXES FOR OXYGEN SEPARATION AND TRANSPORT

BACKGROUND OF THE INVENTION

1. Field of the Invention

The present invention pertains to binuclear metal macrocyclic and macrobicyclic complexes for oxygen separation and transport.

2. Description of the Background

In 1982, Motekaitis et al discovered that the dicobalt complexes of BISDIEN (1) and OBISTREN (2) exhibit an oxygen-carrying capability. The uncomplexed ligands have the formulas:

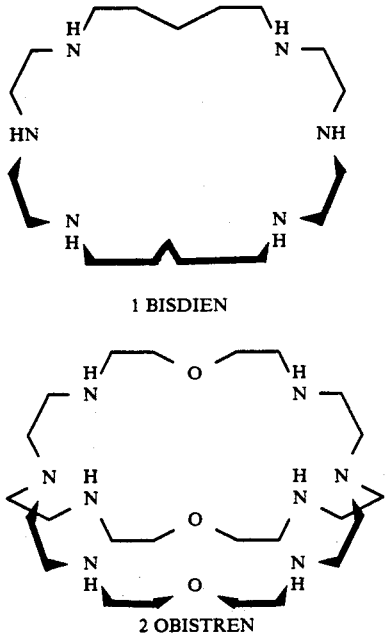

1 BISDIEN

2 OBISTREN

Unfortunately, the potential usefulness of these two complexes has been greatly limited by the expensive multistep process used for their preparation.

More recently, Lehn et al introduced a synthetic method for the preparation of macrocyclic ligands analogous to BISDIEN and OBISTREN However, the processes of Motekaitis et al and Lehn et al have only been used to synthesize a very limited number of ligand compounds, most of which are Schiff base compounds and not polyazamacrocycles or cryptands.

SUMMARY OF THE INVENTION

Accordingly, it is an object of the present invention to provide a method of producing diverse macrocyclic and macrobicyclic cryptand ligands in excellent yields.

It is also an object of the present invention to further provide a method of converting the ligands produced to binuclear metal complexes.

Further, it is an object of the present invention to provide binuclear metal complexes which react reversibly with molecular oxygen, and which may advantageously be used to separate oxygen from gaseous mixtures.

It is a further object of the present invention to provide binuclear metal complexes which, when complexed with oxygen, can be induced to release pure oxygen by relatively small changes in environmental conditions.

DETAILED DESCRIPTION OF THE PREFERRED EMBODIMENTS

Figures 1A, 1B:
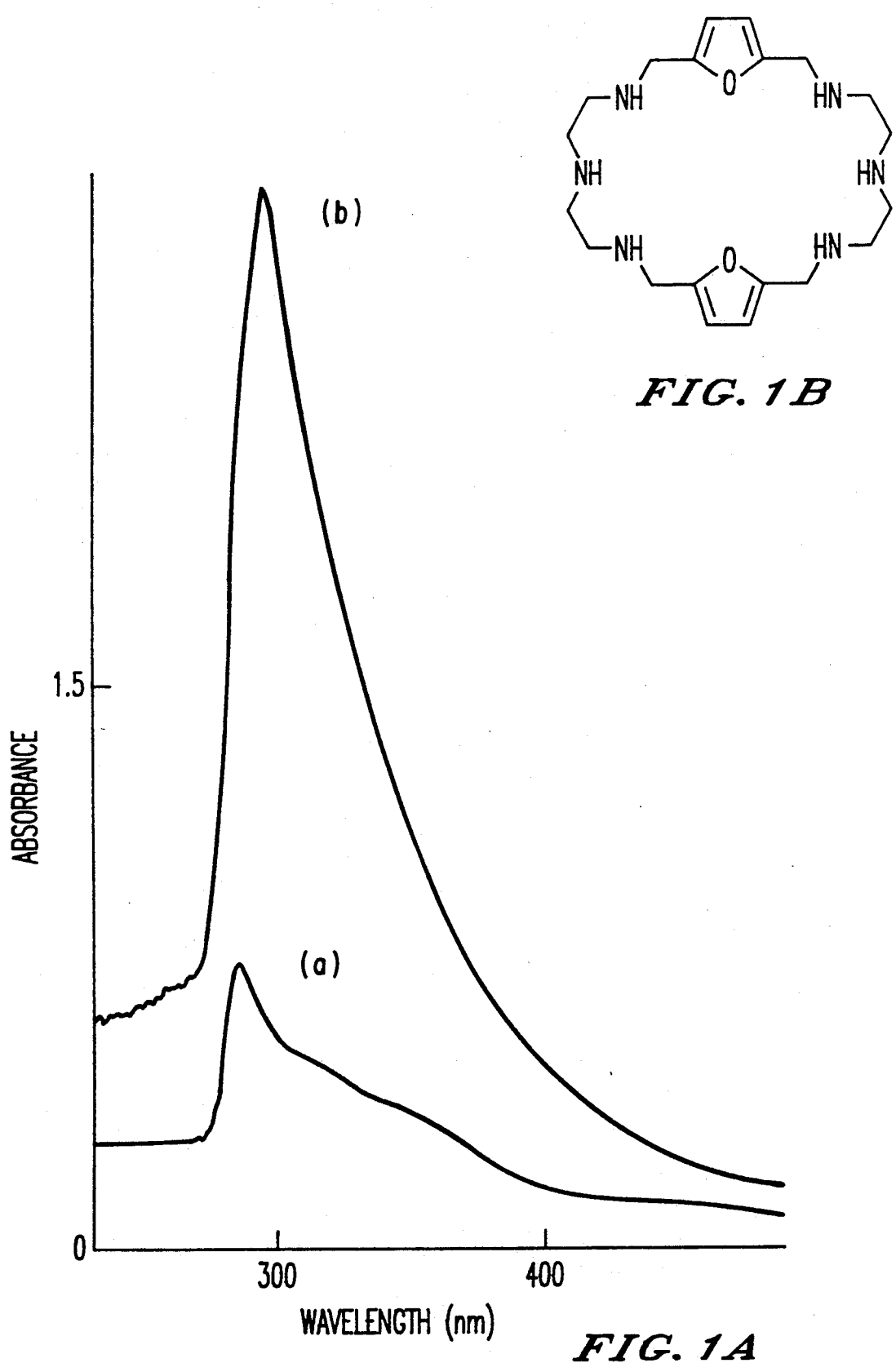
FIG. 1 illustrates the UV-visible spectrum of Co (II)-FUBISDIEN ($7.1 \times 10^{-4}$ M) measured at 25° C. and pH 10.16 (a) the Co (II) complex, (b) the $O_2$ adduct.

In accordance with one aspect of the present invention, binuclear metal complexes are provided which react reversibly with molecular oxygen. Thus, these complexes may be advantageously used to separate oxygen from gaseous mixtures such as air, by complexation of oxygen with the binuclear metal complex, and release of pure oxygen therefrom.

Quite surprisingly, the binuclear metal complexes of the present invention can be conveniently induced to release oxygen in pure form by only small changes in conditions, such as a decrease in pressure, an increase in temperature or, when in solution, by oxidation at an anode. The precise conditions required to effect this result vary from one complex to another.

The complexation of the metal complexes of the present invention with oxygen may be effected either in solution or in the solid state. When in solution, complexation may be effected by passing a gaseous mixture containing oxygen through a solution of the ligand or ligands at a substantially neutral or alkaline pH. When in the solid state, complexation may be effected by exposing the metal complex or complexes directly to the gaseous mixture containing oxygen.

In accordance with another aspect of the present invention, a method of producing diverse macrocyclic and macrobicyclic binucleating ligands is provided. Generally, a dialdehyde is reacted with a poly primary amine in a suitable organic solvent at ambient temperature to form macrocyclic or macrobicyclic ligand compounds by Schiff base condensation. The resulting Schiff base is then reduced to form the corresponding cryptand.

Generally, although the reaction of the dialdehyde and poly primary amine is usually conducted at ambient temperature, temperatures in the range of about 10° C. to about 50° C. may be used. However, a temperature of about room temperature is preferred.

The resulting cryptand may then be mixed with a solution of metal ions to form the corresponding binuclear metal complex.

In accordance with a most important aspect of the present invention, it has been discovered that dialdehydes and bis-primary amines may be condensed to form a tetra-condensation product. This result appears to occur when about two moles of a dialdehyde react with about two moles of a bis-primary amine in accordance with the following general schematic:

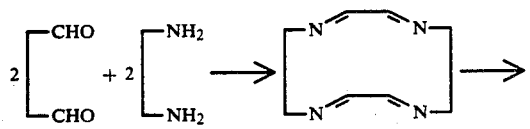

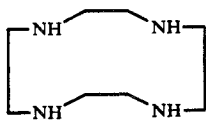

"tetra condensation"

Alternatively, it has also been discovered in accordance with the present invention that dialdehydes and tris-primary amines may be condensed to form a hexa-condensation product. This result appears to occur when about three moles of dialdehyde react with about two moles of tris-primary amine in accordance with the following general schematic:

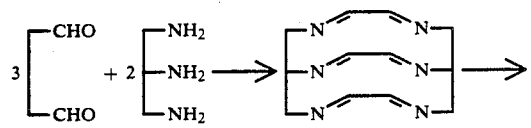

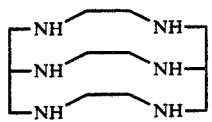

"hexa condensation"

The above stoichiometries which are plausible reaction stoichiometries for the present reactions may be distinguished from the reaction stoichiometries of classical condensations which are represented hereinbelow:

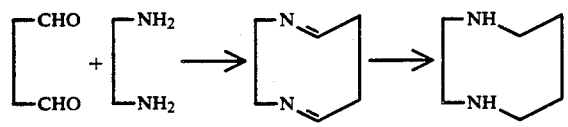

or

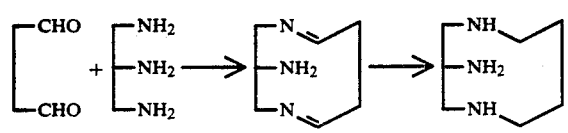

In general, the choice of the poly primary amine will depend upon the condensation pattern. For example, a diamine of the formula:

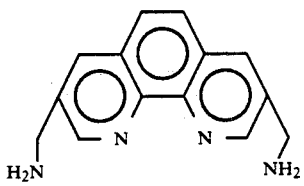

will follow a tetra-condensation pattern when reacted with a dialdehyde because of the rigidity induced by the condensed rings. By contrast, the bis-primary amine equivalent of the formula:

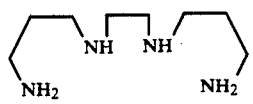

would be expected to follow the classical condensation pattern inasmuch as free rotations are possible which will let the two primary amine groups achieve close proximity to each other, thereby facilitating condensation with two aldehyde groups of the same dialdehyde molecule.

More particularly, the dialdehydes used in the present process have the general formula:

OHC—Q—CHO wherein Q is a $C_1$-$C_4$ alkyl group; a $C_1$-$C_4$ alkyl group, itself, having one or more lower alkyl substituent groups; a vinyl group; a benzene group with either 1,2 or 1,3-substitution; or a pyridine, pyrrole, furan or thiophene ring having 2,5-substitution, wherein each of the above rings are unsubstituted or substituted by lower alkyl groups.

Some of the preferred dialdehydes are those having the formula:

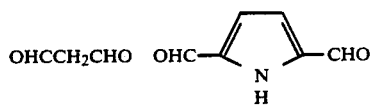

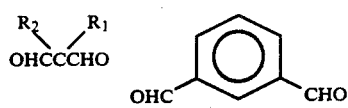

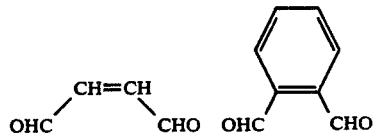

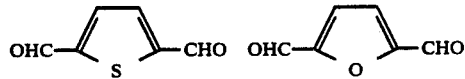

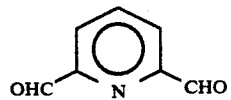

In the above formulas, $R_1$ and $R_2$ are independently each hydrogen, lower alkyl, lower alkoxy, lower alkyl substituted by lower alkyl, phenyl or phenyl substituted by lower alkyl or lower alkoxy. However, other substituents for $R_1$ and $R_2$ may be used provided that they do not interfere with condensation.

The poly primary amines which react with the above dialdehydes are preferably bis- and tri-primary amines. These compounds generally have the formula:

S-(X-NH$_2$)$_n$ wherein n is 2 or 3, and S is a substituted nitrogen or carbon atom, a benzene ring, a pyridine ring or a larger heterocyclic ring system, all of which rings may be either unsubstituted or substituted by lower alkyl groups, and X is a lower alkylene group, preferably a methylene, ethylene or propylene group.

Some of the preferred bis-primary amines of the present invention have the formulae:

[Chemical structures: bis-primary amine with central N-R and two -NH$_2$ arms; bipyridine with two -CH$_2$NH$_2$ groups; propyl analog with central N-R; pyridine with two -CH$_2$NH$_2$ groups; phenanthroline-like structure with two -CH$_2$NH$_2$ groups; m-xylylenediamine H$_2$N-CH$_2$-C$_6$H$_4$-CH$_2$-NH$_2$]

In the above formulas, R is hydrogen, lower alkyl, lower alkyl substituted by lower alkyl, phenyl, pyridine or phenyl and pyridine each substituted by lower alkyl.

Alternatively, some of the preferred tris-primary amines of the present invention have the formulae:

[Chemical structures: TREN; analog of TREN (with H$_3$C-C center); larger macrocyclic tris-amine; 4-amino-1,7-diazaheptane; 1,3,5-tris(aminomethyl)-benzene; tris-amine with H$_3$C-C center]

TREN        analog of TREN 4-amino-1,7-diazaheptane 1,3,5-tris(aminomethyl)-benzene The various dialdehyde compounds and poly primary amines as described above are reacted using a molar ratio of about 10:1 to 1:10, respectively. Thereby, a diverse group of macrocyclic and macrobicyclic binucleating ligands can be synthesized. However, in accordance with the present invention, it is advantageous to use either about a 1:1 molar ratio or 3:2 molar ratio when using bis-primary and tris-primary amines, respectively.

The organic solvents which may be used are those which are capable of solvating dialdehydes and poly primary amines. Such solvents are well known to those skilled in the art and may be readily identified by reference to standard laboratory solubility tables used in organic chemistry. As an example, acetonitrile, methanol dimethylformamide and dimethylsulfoxide may be used as such solvents.

For example, when a dialdehyde of the formula:

[Chemical structure: 2,5-diformylfuran OHC-furan-CHO]

is condensed with diethylenetriamine of the formula:

[Chemical structure: H$_2$N-CH$_2$CH$_2$-N(R)-CH$_2$CH$_2$-NH$_2$]

where R is hydrogen, and the product obtained is reduced, the following furan analog of BISDIEN is obtained:

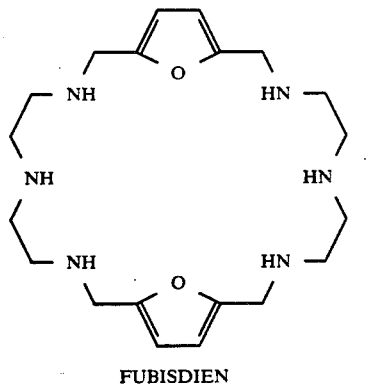

FUBISDIEN

Similarly, when a dialdehyde of the formula:

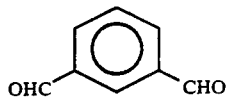

is condensed with diethylenetriamine, and the product obtained is reduced, the following m-xylyl analog of BISDIEN is obtained.

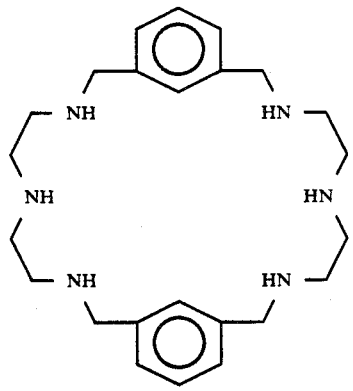

MXBISDIEN

Also, when a dialdehyde of the formula:

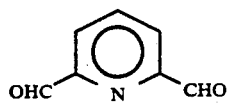

is condensed with diethylenetriamine and the product obtained is reduced, the following pyridyl analog of BISDIEN is obtained:

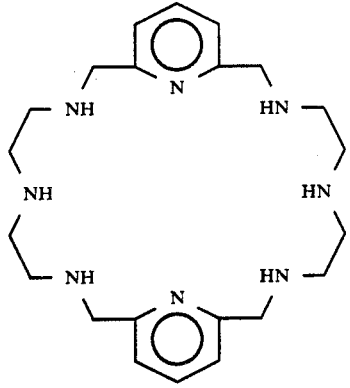

PYBISDIEN

Similarly, the above-mentioned dialdehydes have been condensed with the tris-primary amine TREN of the formula:

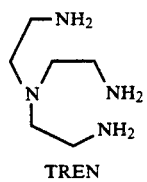

TREN to afford, after reduction, the following respective cryptand macrobicyclic ligands FUBISTREN, MXBISTREN and PYBISTREN.

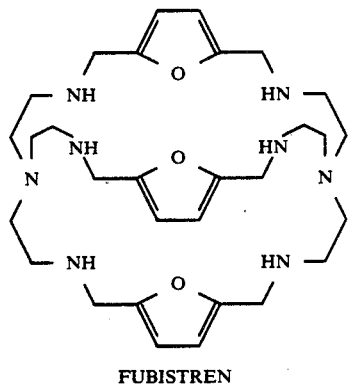

FUBISTREN

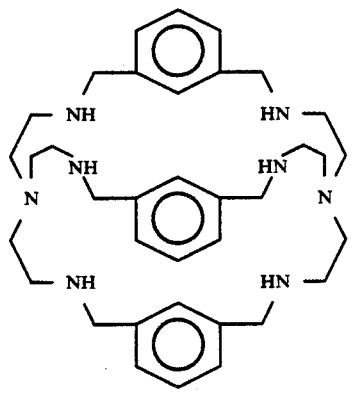

MXBISTREN

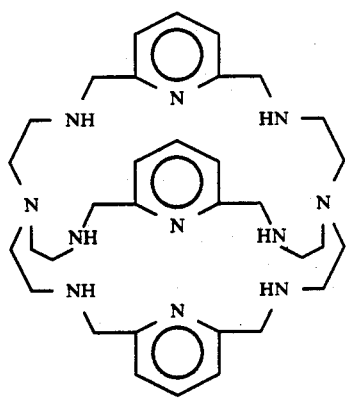

PYBISTREN

The Schiff base product may be reduced using a variety of reducing agents provided that they are relatively selective for imine bonds. Although catalytic hydrogenation may be used, metal hydrides and borohydrides have been found to be particularly advantageous. Of note are the alkali metal hydrides such as NaH and KH, and the alkali metal borohydrides $NaBH_4$ and $KH_4$. It is most preferred, however, to use an alcoholic solution of $NaBH_4$, such as in methanol.

After forming the cryptand macrocyclic and macrobicyclic ligand compounds of the present invention, the corresponding binuclear metal complexes may be prepared by combining the ligand compounds with about 1½ to 3 equivalents of a water-soluble metal (II) salt. Preferably, about two equivalents of a metal (II) salt are combined with one or more of the present ligands in an acidic aqueous solution.

The metal salts which may be used in accordance with the present invention are generally of the metal (II) salts which are capable of forming metal-complexes. Non-limiting and illustrative examples of such salts are the halides, acetates, nitrates, perchlorates and sulfates of $Ni^{+2}$, $Mn^{+2}$, $Fe^{+2}$ and $Cu^{+2}$, for example. However, any metal (II) salt may be used provided that the salt is water-soluble and the metal ion is capable of forming complexes with the ligands of the present invention.

The pH of the solution is then raised by the gradual addition of an alkali metal hydroxide or carbonate or an alkaline earth hydroxide or carbonate. Then, oxygen is passed through the solution under either neutral or alkaline conditions, i.e., a pH of about 7.0 or greater, and the brown coloration of the binuclear metal dioxygen complex appears. The brown coloration is the characteristic color of binuclear metal dioxygen complexes. However, upon reacidification of the solution the brown color disappears due to the dissociation of the binuclear metal dioxygen complexes upon protonation thereof.

Generally, the bound oxygen can be gradually released by gradually lowering the pH, or more quickly released by quickly lowering the pH. It is usually not necessary to decrease the pH to less than about 2 or 3 in order to effect the release of oxygen.

Generally, the extent to which the pH must be raised and then lowered in order to obtain optimal oxygen complexation and release will vary depending upon which ligand is used. However, the optimal alkaline and acidic pH values for any particular ligand used may be readily determined by one of ordinary skill in the art using well-known analytical techniques.

Any acidic reagent may be used to lower pH as long as it is inert with respect to the metal-complexed cryptand and is soluble in the cryptand solution. For example, mention may be made of various organic acids such as acetic acid or citric acid, or mineral acids such as sulfuric acid, nitric acid or hydrochloric acid. Of all reagents, however, the mineral acids are most preferred.

In addition to forming oxygen adducts in solution, in accordance with the present invention, the binuclear metal complexes of the present invention also may, in the form of dry complexes, form oxygen adducts when exposed directly to gaseous mixtures containing oxygen. Generally, the present binuclear metal complexes will form oxygen adducts when exposed to gaseous mixtures containing oxygen, such as air, and will release oxygen when the gas pressure is decreased.

The release of dioxygen may be facilitated by the presence of water vapor in the gaseous mixture used during the $O_2$ adduct formation step.

For example, the binuclear metal complexes of the present invention may be exposed to a air at a pressure of about 1 atm. or greater for a time sufficient to ensure oxygen adduct formation. Generally, several minutes to several hours is adequate. However, the precise time required in order to achieve optimal results will vary from complex to complex. Thereafter, upon reducing the pressure to less than the pressure used for adduct formation, the oxygen adduct will release oxygen. Generally, it is sufficient to reduce the pressure to about one-fourth atm., and it is usually not necessary to reduce the pressure below about 0.07 atm.

Further, for oxygen adduct formation in solution and in the dry state, temperature has an important impact on the oxygen binding equilibria as indicated by the known equation:

$$\Delta G = RT \ln K$$

Thus, one of ordinary skill in the art would be able to determine the precise effect of temperature on any particular binuclear metal complex-oxygen equilibrium.

The formation of the dioxygen complex is evidenced by measurement of the UV-visible spectra in the absence and in the presence of oxygen. In particular, the increase of absorbance between 300 and 400 nm is indicative of dioxygen complex formation because of the intense oxygen to metal charge transfer band which occurs in this wavelength region. The following descriptions will illustrate the same.

Figures 2A, 2B:
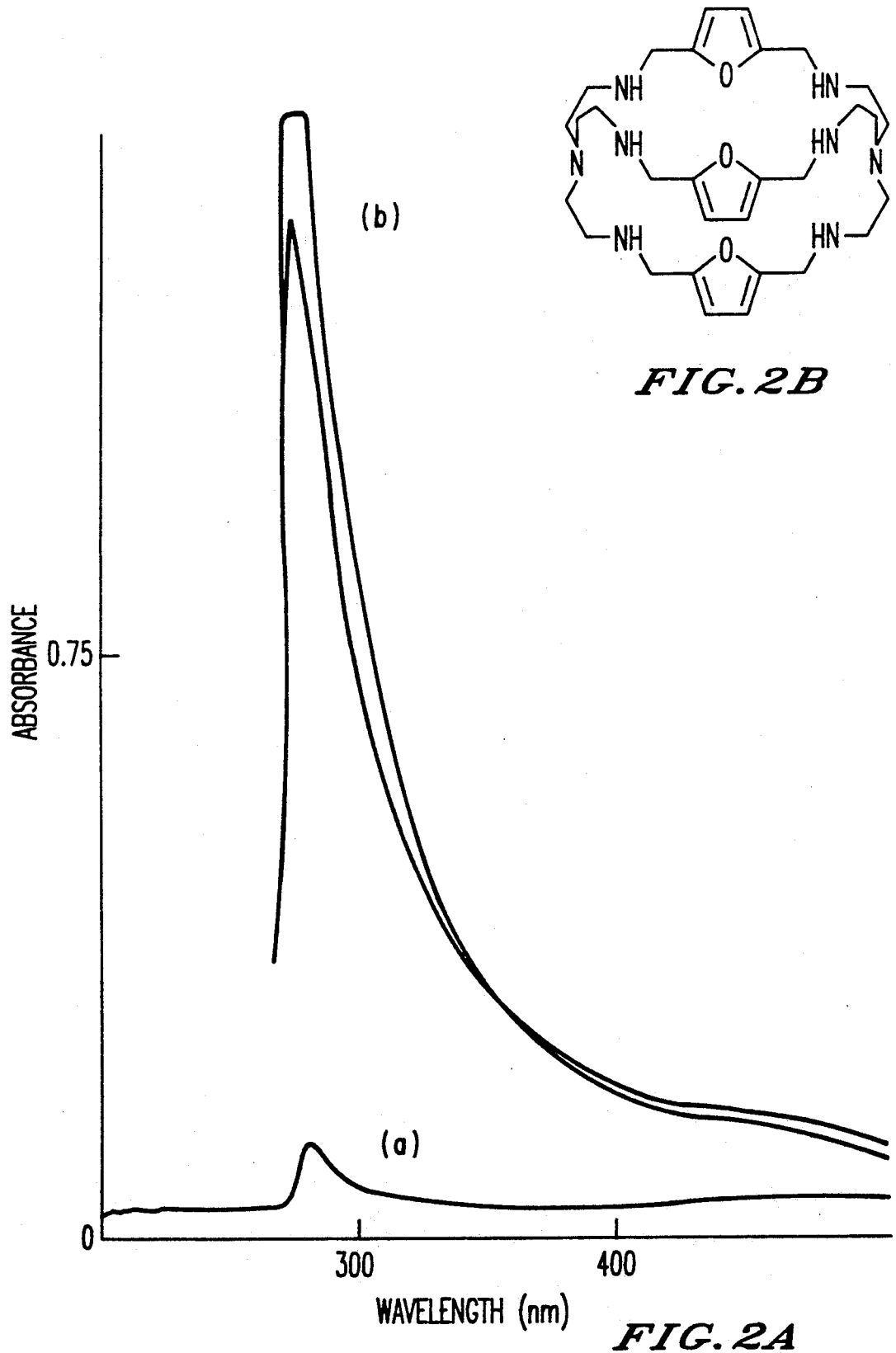
FIG. 2 illustrates the UV-visible spectrum of Co (II)-FUBISTREN ($7.1 \times 10^{-4}$ M) measured at 25° C. and pH 12.70 (a) the Co (II) complex, (b) the $O_2$ adduct.

FIGS. 1A and 2A illustrate the absorbance curves for the dicobalt complexes of FUBISDIEN and FUBISTREN, shown in FIG. 1B and 2B, respectively, in the presence and absence of molecular oxygen.

Figure 3B:
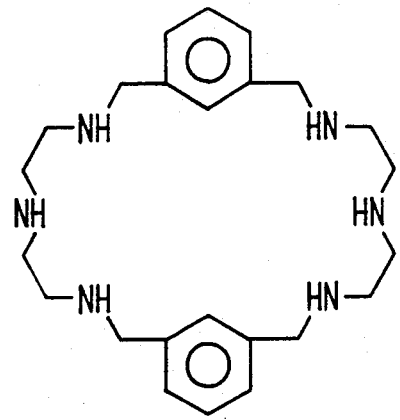
FIG. 3 illustrates the UV-visible spectrum of Co (II)-MXBISDIEN ($4.4 \times 10^{-5}$ M) measured at 25° C. and pH 8.3. (1) under argon, (2) under pure $O_2$.
Figure 3A:
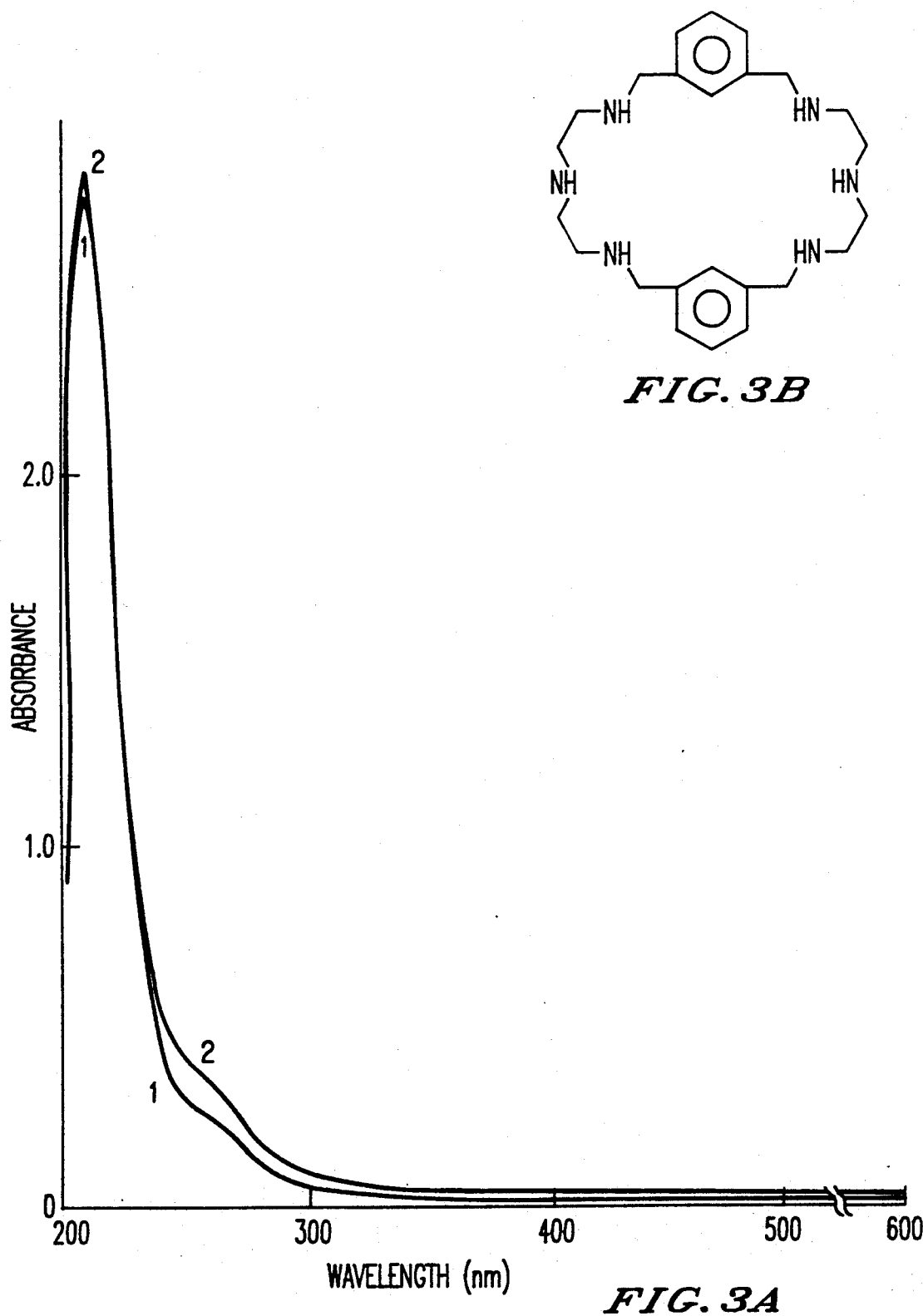
Figure 4B:
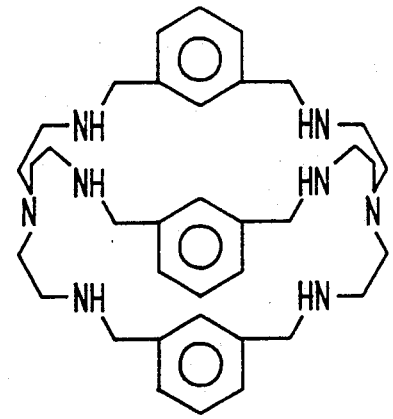
FIG. 4 illustrates the UV-visible spectrum of Co (II)-MXBISTREN ($4.4 \times 10^{-5}$ M) measured at 25° C. and pH 8.8. (1) under argon, (2) under air, (3) under pure $O_2$.
Figure 4A:
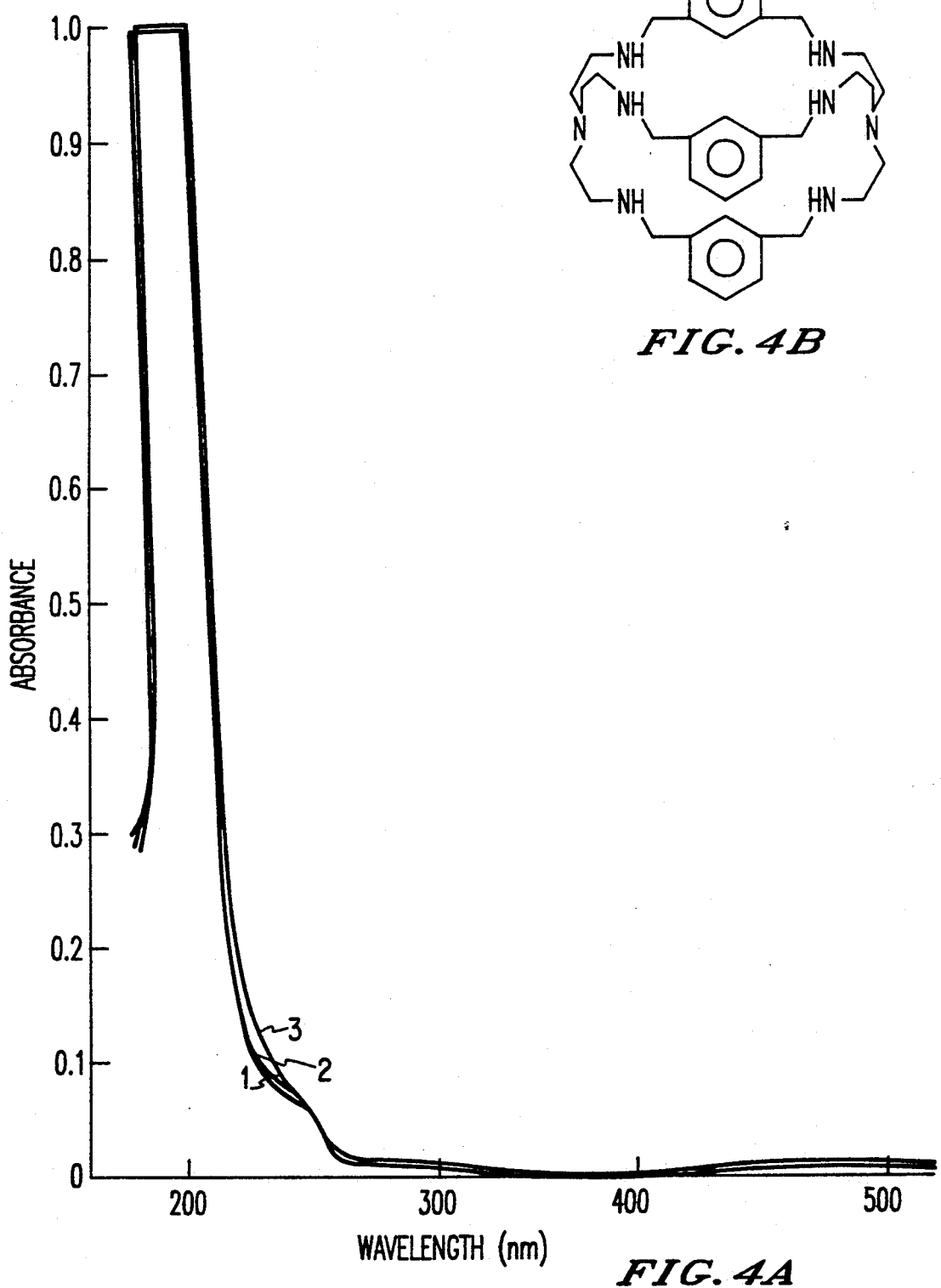

FIGS. 3A and 4A illustrate the absorbance curves for the dicobalt complexes of MYBISDIEN and MXBISTREN, shown in FIGS. 3B and 4B, respectively, in the presence and absence of molecular oxygen.

Figures 5A, 5B:
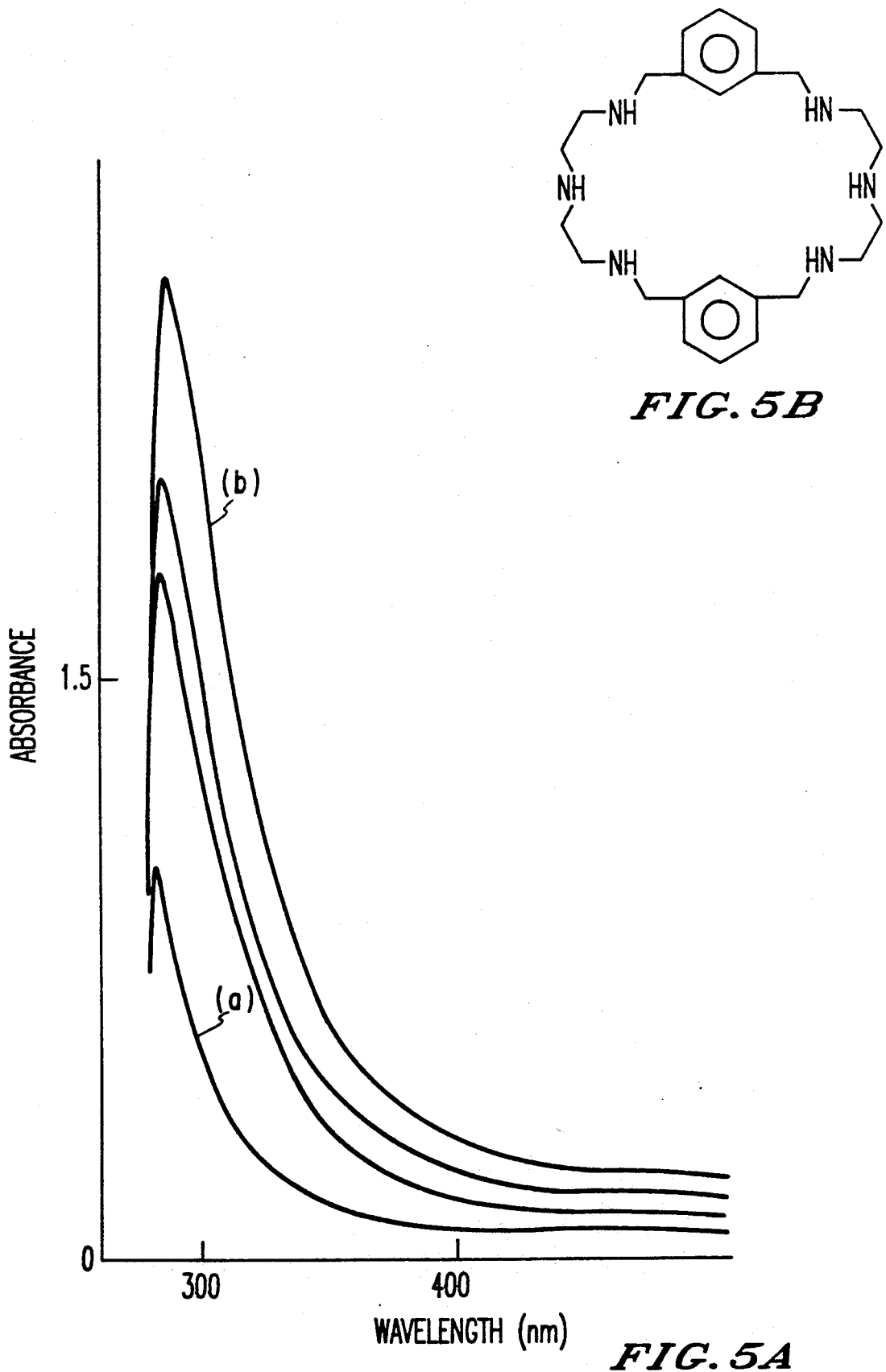
FIG. 5 illustrates the UV-visible spectrum of Co (II)-PYBISDIEN ($7.1 \times 10^{-4}$ M) measured at 25° C. and pH 9.70. (a) the Co (II) complex, (2) the $O_2$ adduct.
Figure 6B:
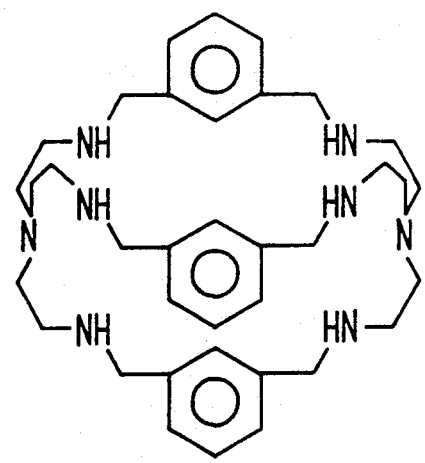
FIG. 6 illustrates the UV-visible spectrum of Co (II)-PYBISTREN ($7.1 \times 10^{-4}$ M) measured at 25° C. and pH 11.60. (a) the Co (II) complex, (2) the $O_2$ adduct.
Figure 6A:
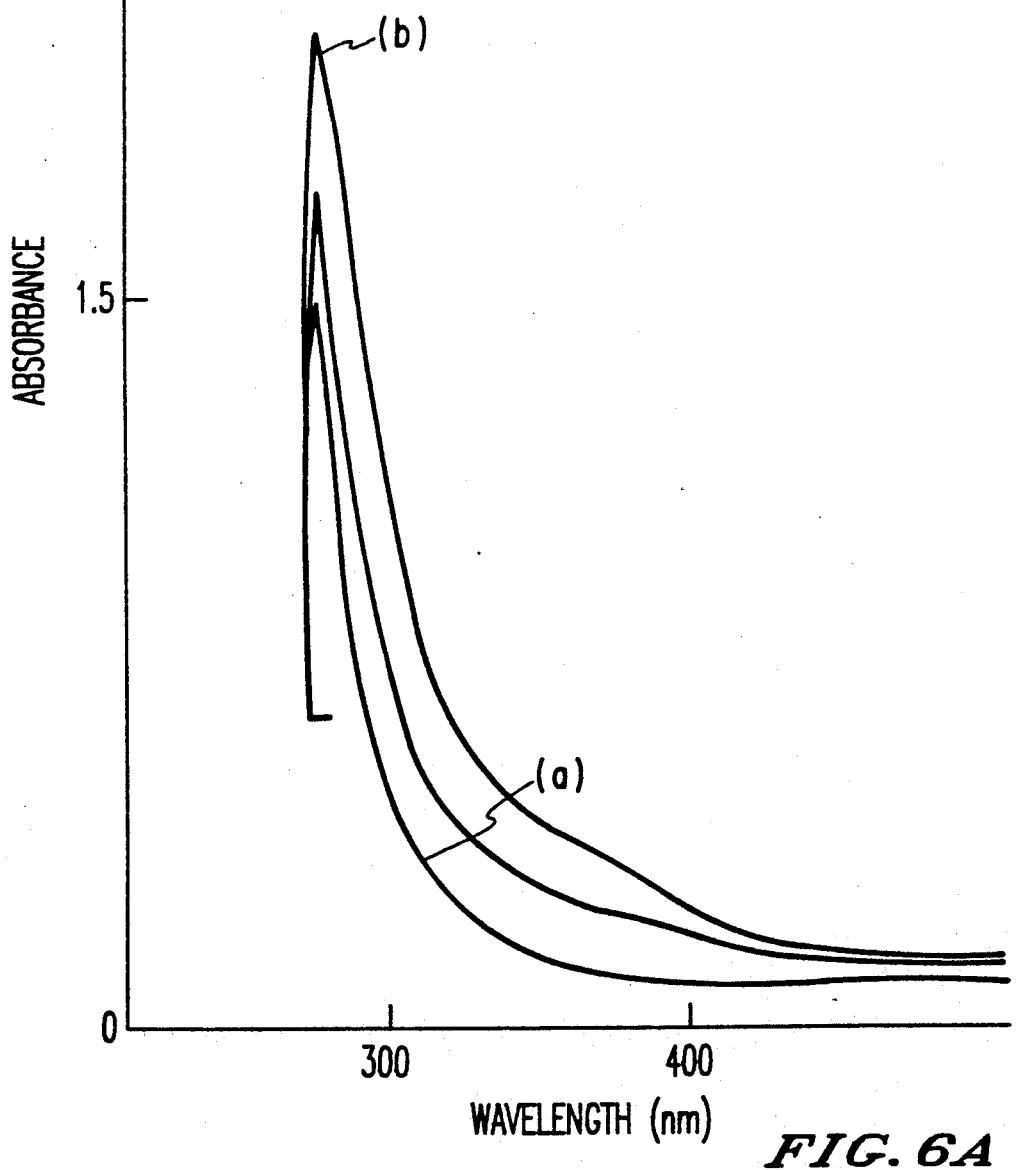

FIGS. 5A and 6A illustrate the absorbance curves for the dicobalt complexes of PYBISDIEN and PYBISTREN, shown in FIGS. 5B and 6B, respectively, in the presence and absence of molecular oxygen.

In general, in accordance with the present invention, oxygen may be recovered from all of the present macrocyclic and macrobicyclic metal complexes by changing the pH when the complex is formed in solution, or by increasing the temperature, or by decreasing the pressure of a gaseous mixture contacting the solid metal complexes of the present invention.

For example, as noted above, the present macrocyclic and macrobicyclic metal complexes can be charged or complexed with oxygen in solution at a pH of substantially about 7.0 or greater. However, when the solution is acidified to a pH of substantially about 7.0 or less, pure oxygen is released from the metal complexes.

Having described the present invention, the same will now be further illustrated by reference to an example which is provided solely for purposes of illustration and is not intended to limit the present invention.

EXAMPLE

Solutions of 2,6-pyridinedicarboxaldehyde and tris(2-aminoethyl) amine in acetonitrile were mixed so as to provide a 3:2 molar ratio of the dialdehyde to the tetramine. The reaction mixture was allowed to stand at room temperature for a day. The Schiff base precipitated and was filtered off. Then, the Schiff base was hydrogenated with sodium borohydride in methanol, and the reaction mixture was evaporated to dryness. The free base was then dissolved in a small amount of 6 M HCl solution and ethanol was added to induce crystallization. The product was then obtained as a colorless crystalline hydrochloride in an overall yield of 40%.

The binuclear metal complexes and oxygen adducts thereof of the present invention may be generally detected and characterized using conventional and well-known techniques of of electron spin resonance (ESR), nuclear magnetic resonance (NMR) spectroscopies and thermogravimetry.

Having now described the present invention, it will be apparent to one of ordinary skill in the art that many changes and modifications may be made to the embodiments described above while remaining within the ambit of the present invention.

What is claimed is:

1. A binuclear metal complex, comprising a metal-complexed ligand, which ligand is formed by the reaction of a dialdehyde and a bis-primary amine or a tris-primary amine, which complex is capable of reacting reversibly with molecular oxygen.

2. The binuclear metal complex according to claim 1, wherein said dialdehyde is selected from the group consisting of a dialdehyde of the formula:

OHCCH$_2$CHO

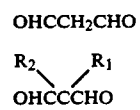

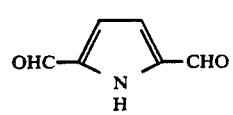

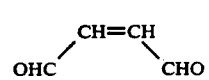

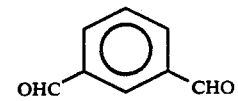

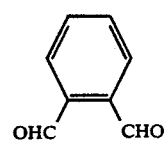

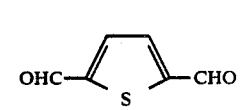

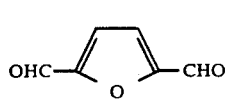 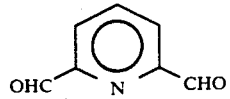

wherein R$_1$ and R$_2$ are independently each hydrogen, lower alkyl, lower alkoxy, lower alkyl substituted by lower alkyl, phenyl or phenyl substituted by lower alkyl or lower alkoxy.

3. The binuclear metal complex according to claim 1, wherein said bis-primary amine is selected from the group consisting of an amine of the formula:

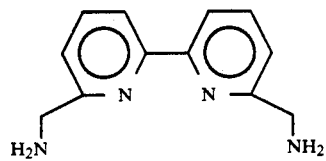

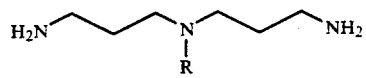

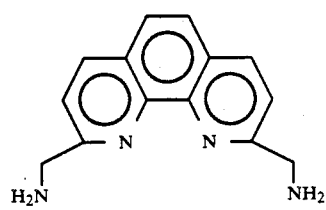

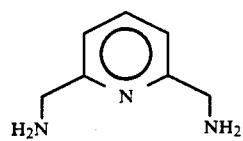

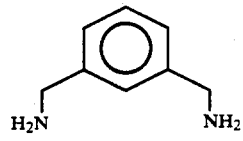

wherein R is hydrogen, lower alkyl, lower alkoxy, lower alkyl substituted by lower alkyl, phenyl or phenyl substituted by lower alkyl and lower alkoxy.

4. The binuclear metal complex according to claim 1, wherein said tris-primary amine is selected from the group consisting of an amine of the formula:

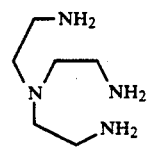 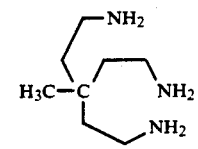

-continued

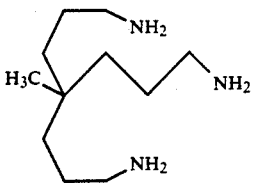

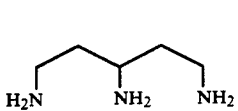

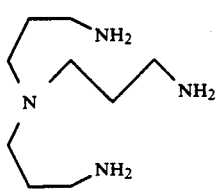

5. The binuclear metal complex according to claim 1, wherein said metal is selected from the group consisting of $Ni^{+2}$, $Mn^{+2}$, $Fe^{+2}$ and $Cu^{+2}$.

6. A method of extracting oxygen from a gaseous mixture containing the same, which comprises:
   a) contacting a binuclear metal complex, comprising a metal-complexed ligand, which ligand is formed by the reaction of a dialdehyde and a bis-primary amine or a tris-primary amine, which complex reacts reversibly with molecular oxygen, with said gaseous mixture containing oxygen, to form a dioxygen adduct with said binuclear metal complex; and
   b) inducing said dioxygen-binuclear metal adduct to release substantially pure oxygen therefrom.

7. The method according to claim 6, wherein said binuclear metal complex is in solid form when contacted with said gaseous mixture.

8. The method according to claim 6, wherein said binuclear metal complex is in solution when contacted with said gaseous mixture.

9. The method according to claim 8, wherein said solid binuclear metal complex is contacted with said gaseous mixture at a pressure and a time at least sufficient to effect oxygen adduct formation.

10. The method according to claim 9, wherein said oxygen adduct is induced to release substantially pure oxygen therefrom by decreasing the pressure to less than said contacting pressure.

11. The method according to claim 8, wherein when said binuclear metal complex in solution is contacted with said gaseous mixture, said solution has a pH of about 7.0 or greater to effect oxygen adduct formation.

12. The method according to claim 11 wherein said oxygen adduct is induced to release substantially pure oxygen therefrom by decreasing the pH to less than said contacting pH.

* * * * *